United States Patent
Patnaik et al.

(10) Patent No.: US 6,713,568 B1
(45) Date of Patent: Mar. 30, 2004

(54) COMPOSITION AND PROCESS FOR PREPARING BIOCOMPATIBLE POLYMER COATINGS

(75) Inventors: Birendra K. Patnaik, Chester, NJ (US); Richard J. Zdrahala, Eden Prairie, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/136,655

(22) Filed: Aug. 19, 1998

Related U.S. Application Data

(63) Continuation-in-part of application No. 08/713,803, filed on Sep. 13, 1996, now Pat. No. 5,855,618.

(51) Int. Cl.$^7$ .................................................. C08F 8/32
(52) U.S. Cl. ........................ 525/379; 525/382; 525/454
(58) Field of Search ................................ 525/379, 382, 525/454

(56) References Cited

U.S. PATENT DOCUMENTS

| | | |
|---|---|---|
| 4,229,838 A | 10/1980 | Mano |
| 4,331,697 A | 5/1982 | Kudo et al. |
| 4,521,564 A | 6/1985 | Solomon et al. |
| 4,600,652 A | 7/1986 | Solomon et al. |
| 4,613,517 A | 9/1986 | Williams et al. |
| 4,642,242 A | 2/1987 | Solomon et al. |
| 4,678,660 A | 7/1987 | McGary et al. |
| 4,713,402 A | 12/1987 | Solomon |
| 4,720,512 A | 1/1988 | Hu et al. |
| 4,786,556 A | 11/1988 | Hu et al. |
| 4,973,493 A | 11/1990 | Guire |
| 4,979,959 A | 12/1990 | Guire |
| 5,028,597 A | 7/1991 | Kodama et al. |
| 5,061,777 A | 10/1991 | Yoda et al. |
| 5,077,352 A | 12/1991 | Elton |
| 5,077,372 A | 12/1991 | Hu et al. |
| 5,132,108 A | 7/1992 | Narayanan et al. |
| 5,134,192 A | 7/1992 | Feijen et al. |
| 5,171,264 A | 12/1992 | Merrill |
| 5,244,654 A | 9/1993 | Narayanan |
| 5,258,041 A | 11/1993 | Guire et al. |
| 5,366,518 A | 11/1994 | DeRosa et al. |
| 5,409,696 A | 4/1995 | Narayanan et al. |
| 5,436,291 A | 7/1995 | Levy et al. |
| 5,451,424 A | 9/1995 | Solomon et al. |
| 5,728,751 A | 3/1998 | Patnaik |

FOREIGN PATENT DOCUMENTS

| | | |
|---|---|---|
| EP | 0 263 184 A1 | 4/1988 |
| EP | 0 404 515 A2 | 12/1990 |
| WO | WO 89/05616 | 6/1989 |
| WO | WO 90/00343 | 1/1990 |
| WO | WO 91/15952 | 10/1991 |
| WO | WO 91/19521 | 12/1991 |

OTHER PUBLICATIONS

Heparin Immobilization onto Segmented Polyurethaneurea Surfaces–Effect of Hydrophilic Spacers, by Ki Dong Park, Teruo Okano, Chisato Nojiri, and Sung Wan Kim, Journal of Biomedical Materials Research, vol. 22, 977–992 (1988).

SPUU–PEO–Heparin Graft Copolymer Surfaces, Patency and Platelet Deposition in Canine Small Diameter Arterial Grafts by Won Gon Kim Ki Dong Park, Syed F. Mohammad, and Sung Wan Kim, 37:M148–149 (1991).

Synthesis and Characterization of SPUU–PEO–Heparin Graft Copolymers, by Ki Dong Park, Ai Zhi Piao, Harvey Jacobs, Teruo Okano and Sung Wan Kim, Journal of Polymer Science: Part A: Polymer Chemistry; vol. 29, pp. 1725–1737 (1991).

PEO–Modified Surfaces–In Vitro, Ex Vivo, and In Vivo Blood Compatibility by Ki Dong Park and Sung Wan Kim Poly (Ethylene Glycol) Chemistry: Biotechnical and Biomedical Applications, pp. 283–301 (1992).

In Vivo Nonthrombogenicity of Heparin Immobilized Polymer Surfaces by Chisato Nojiri, Ki Dong Park, David W. Grainger, Harvey A. Jacobs, Teruo Okano, Hitoshi Koyanagi, and Sung Wan Kim, pp. M168–M172, ASA10 Trans (1990).

Heparin Immobilization by Surface Amplification, Ai–Zhi Piao, Harvey A. Jacobs, Ki Dong Park, and Sung Wan Kim, ASAIO Journal 1992, Slide Forum 26, Biomaterials/Surface Treatments, ppg. M638–M643.

*Primary Examiner*—Bernard Lipman
(74) *Attorney, Agent, or Firm*—Kenyon & Kenyon

(57) ABSTRACT

Disclosed are bio-active polymer coatings. More particularly, improved bio-active polymer coating are disclosed which include bio-active molecules attached to polymer backbones via spacers having reactive nitrogen groups. Also disclosed are novel reaction schemes for producing same.

13 Claims, No Drawings

COMPOSITION AND PROCESS FOR PREPARING BIOCOMPATIBLE POLYMER COATINGS

CROSS-REFERENCE TO RELATED APPLICATION

The present application is a continuation-in-part co-owned U.S. Ser. No. 08/713,803 filed Sep. 13, 1996 now U.S. Pat. No. 5,855,618 which is incorporated by reference herein.

FIELD OF INVENTION

The present invention relates generally to bio-active polymer coatings. More particularly, the present invention relates to an improved bio-active polymer coating including a bio-active molecule attached to a reactive carbon atom in a polymer backbone via a spacer having reactive nitrogen groups.

BACKGROUND OF THE INVENTION

It is well known to use bio-active materials to coat structures to be introduced into a living system. Over the last 30 years, research into this area has become increasingly important with the development of various bio-compatible articles for use in contact with blood, such as, for example, vascular grafts, artificial organs, endoscopes, cannulas, and the like.

While various materials have been used to make such articles, synthetic polymers have been increasingly popular as the preferred materials due to their anti-thrombogenic and good mechanical properties. For example, polyurethane is a useful and effective material with a variety of clinical applications. Although synthetic polymers, such as, PTFE and polyurethane, are less thrombogenic than earlier materials, thrombus formation is still a problem. A thrombus is the formation of a solid body composed of elements of the blood, e.g., platelets, fibrin, red blood cells, and leukocytes. Thrombus formation is caused by blood coagulation and platelet adhesion to, and platelet activation on, foreign substances. Thus, thrombus formation is a serious complication in surgery and clinical application of artificial organs.

Various anti-thrombogenic agents, such as, heparin, have been developed and incorporated into bio-compatible articles to combat thrombus formation. In a living system, heparin inhibits the conversion of a pro-enzyme (prothrombin) to its active form (thrombin). Thrombin catalyzes a complicated biochemical cascade which ultimately leads to the formation of a thrombus.

Infection is also a serious concern for articles to be implanted into a host organism. Bacterial, viral and other forms of infection may lead to life-threatening complications when an article is implanted into a host organism. Thus, binding of an anti-infection agent to a surface of an implantable article can reduce the risk of infection when an article is introduced into a host organism.

The art is replete with various procedures for grafting bio-active molecules onto polymer surfaces to prevent thrombus formation and/or infection. For example, biocompatible polymer surfaces have been described with various benefits including decreased thrombogenicity, increased abrasion-resistance and improved hydrophilic lubricious properties. Alternatively, preparing polymeric surfaces to receive bio-active agents by plasma treatment is also well known in the art.

Various polyurethane coatings to which bio-active agents are added have also been described. For example, bio-active agents directly bound to the polymer backbone of a polymer coating material are known. Also, polymer coatings are described that include either covalently or ionically binding bio-active agents to substrate surfaces. For example, photochemical reactions are described which covalently bind bio-active agents to substrate surfaces. Also, quartenary ammonium reagents are described which ionically bind a bio-active agent to a substrate. In polyurethane coatings, various spacer molecules that link bio-active agents to polymer substrates have been described by several studies. These studies indicate that bio-active agents, such as, for example, heparin bound to polymer coatings, retain more of their activity if they are tethered away from the surface of an article by a spacer.

Various substrate surfaces have previously been described that are suitable for introduction into a biological system. For example, Yoda et al. in U.S. Pat. No. 5,061,777 disclose that polyurethanes and polyurethaneureas containing both hydrophilic and hydrophobic polyether segments are more anti-thrombogenic than substrates produced from either a hydrophilic or a hydrophobic polyol exclusively. Similarly, Elton in U.S. Pat. No. 5,077,352 discloses a method of forming a mixture of an isocyanate, a polyol and a poly (ethylene oxide) in a carrier liquid. This mixture is then heated and cured to form a coating of a polyurethane complexed with a poly(ethylene oxide) having good adherence to a substrate and good anti-friction properties.

A significant limitation of these bio-compatible polymer surfaces, however, is that they are not completely biocompatible. Thrombus formation and infection continue to pose problems when an article is implanted within a host using these bio-compatible polymer surfaces. Thus, various alternative methods have been described for preparing the surface of an article to be implanted in a host organism to accept bio-active agents. Plasma treatment of substrate surfaces is one such method.

For example, Hu et al. in U.S. Pat. No. 4,720,512 disclose a method for imparting improved anti-thrombogenic activity to a polymeric support structure by coating it with an amine-rich material, e.g., a polyurethaneurea, introducing hydrophobic groups into the amine-rich surface coating through plasma treatment with fluorine compounds, and covalently bonding an anti-thrombogenic agent to the hydrophobic amine-rich surface. Similarly, Hu et al. in U.S. Pat. No. 4,786,556 disclose substituting siloxane and silazane compounds during the plasma treatment step of the '512 patent for the previously disclosed fluorine compounds. See also, Narayanan et al. in U.S. Pat. No. 5,132,108 and 5,409,696 and Feijen et al. in U.S. Pat. No. 5,134,192 for other examples of plasma treating substrates prior to introduction of a bio-active molecule.

These preceding methods for plasma treating a substrate surface are limited in their scope because they only work with certain substrates. Thus, they do not provide a general purpose coating composition that can bind to a variety of substrate surfaces. In an alternate approach, however, various methods have been described for binding bio-active agents directly to substrate surfaces.

For example, Solomon et al. in U.S. Pat. No. 4,642,242 disclose a process for imparting anti-thrombogenic activity to a polyurethane polymer material by coating a support structure with a protonated amine-rich polyurethaneurea, activating the amine moiety with an alkaline buffer, and covalently linking an anti-thrombogenic agent, e.g., heparin, to the polyurethaneurea with a reducing agent.

Hu et al. in U.S. Pat. No. 5,077,372 disclose a medical device having a hemocompatible polyurethaneurea surface coating that is produced by reacting a diisocyanate, a polyamine and a mixture of fluorinated and nonfluorinated polyols, and an anti-thrombogenic agent covalently linked to the amino groups of the polyurethane coating. These coating reactions and heparinizations are carried out directly on the device's surface.

Bio-active agents bound directly to polymer backbones suffer from several limitations. First, because these bio-active agents are directly linked to the polymer backbone, their in vivo mobility is decreased. Second, the process of linking the bio-active agent to the polymer backbone may diminish the number of functional binding sites on the bio-active agent. Third, the bio-active agent's close proximity to the polymer backbone limits its ability to interact with its physiological substrates. Thus, for all of these reasons, coatings containing bio-active molecules bound directly to the polymer backbone are limited by the bio-active agent's decreased activity.

Accordingly, alternative methods have been developed for binding bio-active molecules to substrate surfaces. In particular, methods for ionically binding bio-active agents to a substrate via a quaternary ammonium compound have been described. See for example, Mano in U.S. Pat. No. 4,229,838, Williams et al. in U.S. Pat. No. 4,613,517, McGary et al. in U.S. Pat. No. 4,678, 660, Solomon et al. in U.S. Pat. No. 4,713,402, and Solomon et al. in U.S. Pat. No. 5,451,424.

These methods, however, are severely limited because the bio-active agent is leached over time from the surface of the substrate. Thus, the protection afforded by the ionically bound bio-active agent to the substrate surface is transient at best. Accordingly, more permanent methods for binding bio-active molecules to substrate surfaces have also been developed. These methods include covalently binding a bio-active molecule, either directly, or via a spacer molecule, to a substrate surface.

For example, photochemical reactions have been described for preparing substrate surfaces to receive anti-thrombogenic agents. Kudo et al. in U.S. Pat. No. 4,331,697 disclose a method for imparting anti-thrombogenic activity to a biomedical material by directly linking a heparin derivative to the surface of the material via actinic radiation. Similarly, Kudo et al. also disclose coating a surface of a biomedical material with a polymer having a carboxylic acid halide group and/or a carboxylic anhydride functional group as a side chain that can react with a heparin derivative.

Alternatively, Guire et al. in U.S. Pat. Nos. 4,973,493 and 4,979,959 disclose methods for binding bio-active molecules to substrates using a linking moiety with functionalized end groups preferably that are activated by different signals. The linking moiety can covalently bind a bio-active molecule upon introduction of a first activation signal which activates the first functionalized end group. The linking moiety is further capable of covalently binding to the substrate upon introduction of a second, different, signal (photochemical) which activates the second functionalized end group. Similarly, Guire et al. in U.S. Pat. No. 5,258,041 further define the spacer molecule of their '493 and '959 patents.

Lastly, Bichon et al. in U.S. Pat. No. 4,987,181 disclose a substrate having an adhesive film with anti-thrombogenic properties on its surface. This adhesive film is an olefinic copolymer having carboxylic side chains of the formula $O=CH—NH—(CH_2)_n—NH—CH_2—R$, wherein R is a heparin molecule or a depolymerization fragment of a heparin molecule. The adhesive film is deposited onto the substrate via photo-initiated polymerization of a suitable monomer. Thus, heparin, or a fragment thereof, is covalently linked to the substrate via an amine spacer.

Although spacer molecules provide a means for optimizing the bio-activity of bio-agents bound to substrate surfaces, several problems persist in the photochemical reactions used to bind these bio-active molecules via spacers to substrate surfaces. Included among these problems are the ability of the bio-active molecule to withstand the photochemical signal used to bind it to the substrate surface, as well as the ability of the substrate to withstand photoradiation. For example, inert polymeric substrates, e.g., polytetrafluoroethylene, degrade when exposed to photochemical reactions and cannot be used therewith. Thus, attempts have been made to use spacer molecules to bind bio-active agents to substrate surfaces without photochemical reactive groups.

For example, in a four step process, Park et al. disclose immobilizing heparin onto a commercial preparation of a segmented polyetherurethaneurea (PUU) using hydrophilic poly(ethylene oxide) (PEO) spacers of different molecular weights. Their method includes (1) coupling hexamethyldiisocyanate (HMDI) to a nitrogen atom in the urethane linkage of a segmented polyurethaneurea backbone through an allophanate/biuret reaction between the urethane/urea-nitrogen proton and one of the isocyanate groups on the HMDI. Next, (2) the free isocyanate groups attached to the backbone are then coupled to a terminal hydroxyl group on a PEO to form a PUU-PEO complex. Next (3) the free hydroxyl groups of the PUU-PEO complex are treated with HMDI to introduce a terminal isocyanate group. Finally, (4) the NCO functionalized PUU-PEO is then covalently bonded to reactive functional groups on heparin (—OH and —NH$_2$) producing a PUU-PEO-Hep product. K. D. Park and S. W. Kim, "PEO-Modified Surfaces-In Vitro, Ex Vivo and In Vivo Blood Compatibility", in Poly(Ethylene Glycol) Chemistry: Biotechnical and Biomedical Applications 283 (J. Milton Harris ed. 1992). This method will be referred to hereinafter as the "Park Method."

All of these disclosures have addressed substrate surfaces and/or coatings therefor which can exist within biological systems and in particular, can increase the anti-thrombogenicity of the surface of, e.g., medical articles. These reactions are generally slow, polymer-specific, multi-step syntheses, and are characterized by side reactions which lead to low yields and formation of cross-linked polymers. In addition, these reactions cannot be universally applied to substrate surfaces. Thus, in particular, there is a need for a bio-active coating and process that can be used with a broad spectrum of substrate surfaces. In addition, there is a need particularly for a coating process that uses a spacer having reactive nitrogen groups to maximize the bio-activity of the bio-active agent. There is also a need for a simplified bio-active coating process that provides a higher yield of polymer with negligible cross-linking in a shorter period of time. The present invention is directed toward providing a solution therefor.

SUMMARY OF THE INVENTION:

The present invention relates to a bio-active coating composition that includes a first reaction in which a bio-compatible polymer backbone is reactive with a spacer having at least one reactive nitrogen group at its first and second ends in the presence of a first dehydrating agent. The polymer backbone has a reactive functionality selected from the group of carboxylic acid functional groups, derivatives thereof and carbon atom-containing functional groups. In this reaction, one of the reactive nitrogen groups reacts with one or more carbon atoms in the reactive functionality of the polymer backbone to form a covalent bond between the spacer and the polymer backbone. This coating composition includes a second reaction in which a bio-active agent is reacted with an unreacted nitrogen group of the spacer in the presence of a second dehydrating agent to covalently bind the bio-active agent to the spacer.

In another embodiment, a coating composition is provided that includes a polymeric structure defined by a bio-compatible polymeric backbone having at least one pendant moiety defined by:

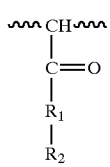

(I)

wherein $R_1$ is a spacer group that includes oxygenated polyolefins, aliphatic polyesters, polyamino acids, polyamines, hydrophilic polysiloxanes, hydrophilic polysilazanes, hydrophilic acrylates, hydrophilic methacrylates, linear and lightly branched polysaccharides; and $R_2$ is a bio-active agent including antithrombogenic agents, antibiotic agents, antibacterial agents, antiviral agents, their pharmaceutical salts and mixtures thereof.

In another embodiment, a method for preparing a bio-active polymer coating is provided wherein a bio-active group is covalently bonded through a spacer to a polymer backbone. This method includes providing a prepolymer backbone having a reactive functionality selected from carboxylic acid groups, derivatives thereof and carbon atom-containing functional groups and forming a pendant group off of the prepolymer backbone by reacting the prepolymer with a spacer having reactive nitrogen groups. In this reaction, a carbon atom of the reactive functionality of the prepolymer forms a covalent bond with a reactive nitrogen group of the spacer in the presence of a first dehydrating agent. An unreacted nitrogen group of the spacer is further reacted with a bio-active agent in the presence of a second dehydrating agent to covalently bond the bio-active agent to the pendant group.

In a further embodiment, a bio-active coating is provided. This coating includes a bioactive coating composition having a biocompatible polymer backbone, a spacer group and a bio-active agent. In this coating composition, the bio-active agent is pendant from the polymer backbone through the spacer group and the spacer group is covalently bonded to the polymer backbone through a reactive carbon atom in the polymer backbone.

The present invention will be more fully understood by a reading of the section entitled "Detailed Description of the Invention".

DETAILED DESCRIPTION OF THE INVENTION

In accordance with the present invention, novel bio-active coatings and their use in developing anti-thrombogenic and/or anti-infective articles are provided. More particularly, new reaction schemes are provided for the synthesis of heparinized polymers, including polyurethanes. Also provided are methods for using the heparinized polymers as anti-thrombogenic coatings on, e.g., small caliber ePTFE vascular grafts.

In the present invention, the polymer or prepolymer backbone may be chosen from any number of useful polymers including poly(urethane), poly(carbonate), polyester and polyether materials provided the requisite functionality is present. Desirably, the polymeric backbone is a polytetramethyleneoxide-based aromatic polyurethaneurea with mixed aliphatic and cycloaliphatic diamine chain extenders. More desirably, the polymer backbone is a polyesterurethaneurea. For example, one useful polyurethane is a commercially available segmented polyurethaneurea known as BIOSPAN® available from the Polymer Technology Group, Inc., Emeryville, Calif.

Desirably, the polymeric structure takes the form of a "comb" configuration, whereby multiple pendant moieties emanate from the backbone like teeth on a comb. These moieties carry at their free terminal end the bio-active agent, which is tethered away from the polymer backbone to make the bio-active agent more accessible to blood, and concurrently to protect against the formation of thrombi.

In the present invention, all of the reactions which add to the polymer backbone take place off of one or more reactive carbon atoms present in the backbone. This is in contrast to prior art coatings and processes which are limited to nitrogen atom-containing polymers, such as, Biomer®, wherein all additions to the polymer take place off of a reactive nitrogen atom in the urethane linkage thereof. See, for example, Park and Feijen supra.

The ability to add to reactive carbon atoms rather than nitrogen atoms in the present polymer backbones is particularly advantageous over previously disclosed polymer coatings because the composition and structure of the final coatings of the present invention are more controllable and reproducible. Moreover, the present invention is not limited to nitrogen atom-containing polymers, such as polyurethaneurea, and accordingly, can be used in conjunction with a wide variety of substrates. In addition, the properties of the bio-active coatings of the present invention can be varied easily, e.g., biostability, hydrophilicity etc. Also, the methods of synthesizing the present bio-active coatings are more efficient and take less time than previously disclosed methods. Another advantage of the present invention is that the reactions may be carried out at lower temperatures. Importantly, the reaction schemes of the present invention form fewer cross-links and provide higher polymer yields than previously described methods.

A composition of the invention was synthesized by reacting a polyol and a methyl diisocyanate to form a prepolymer. This prepolymer was reacted with a chain extender in the presence of a saturated carboxylic acid. Desirably, the saturated carboxylic acid is

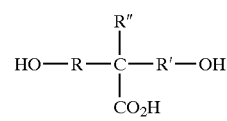

where R is an alkyl of 1–10 carbon atoms; R' is an alkyl of 1–10 carbon atoms; and R" is an alkyl or aryl of 1–10 carbon atoms. In one embodiment, R=R'=CH and R" =CH$_3$. Desirably, the chain extender is butanediol (BDO). The resulting product was a polyurethane polymer containing carboxylic acid functionality (I). This polymer was then added to a hydrophilic amine-terminated poly(ethylene oxide) (II) in the presence of a dehydrating agent as indicated below:

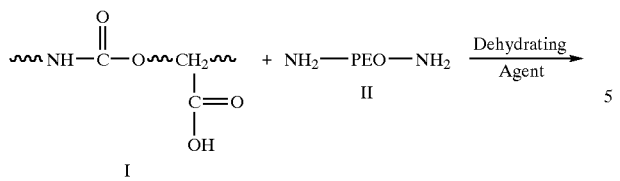

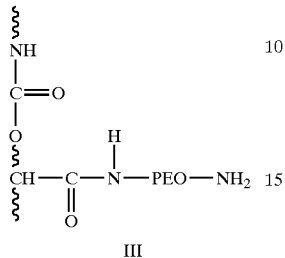

The product (III) of the reaction indicated above is a polymer-spacer complex characterized by an amide linkage between the spacer and the polymer and an amine group on the free terminal end of the spacer. A bio-active agent, such as heparin, is then covalently bonded to the polymer-spacer complex in the presence of a dehydrating agent, such as, EDC, as indicated below:

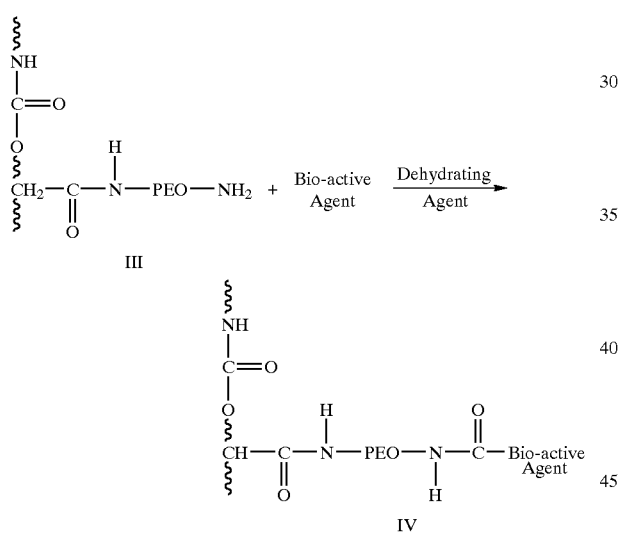

The product (IV) of the reaction indicated above is characterized by an amide linkage between the spacer and the bio-active molecule, e.g., heparin. Thus, in this embodiment, the reaction product (IV) is characterized by amide linkages between its respective units, i.e., between the polymer backbone and the spacer, and between the spacer and the bio-active agent. This composition and its method of synthesis will be referred to hereinafter as "Inventive Embodiment I."

In an another embodiment of this invention, a polyol and a diisocyanate were reacted to form a prepolymer. This prepolymer was reacted with a chain extender in the presence of an unsaturated carboxylic acid. The chain extender can be any internally saturated alpha-omega-dicarboxylic acid, such as, for example oleic or linoleic acids. Desirably, the chain extender is BDO. Thus, in this embodiment, an unsaturated functionality is substituted for the carboxylic acid group of Inventive Embodiment I. Preferably the unsaturated functionality is:

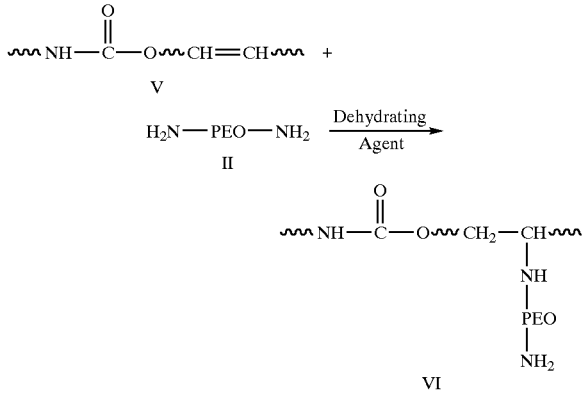

The resulting unsaturated polymer was formed as illustrated below (V). This polymer was then reacted with a hydrophilic amine-terminated poly(ethylene oxide) (II) in the presence of a dehydrating agent as indicated below:

The product (VI) of the reaction indicated above is a polymer-spacer complex characterized by an amine linkage between the spacer and the polymer. A bio-active agent then is grafted to the polymer-spacer complex in the presence of a dehydrating agent, such as, EDC as indicated below:

The product (VII) of the reaction indicated above is characterized by an amide linkage between the spacer and the bio-active molecule. Thus, in this embodiment, the reaction product (VII) is characterized by different linkages between its respective units, i.e., an amine linkage between the polyurethane backbone and the spacer and an amide linkage between the spacer and the bio-active agent. This composition and its method of synthesis will be referred to hereinafter as Inventive Embodiment II.

The dehydrating agent used in the present invention may be any dehydrating agent that can facilitate these reactions such as, for example, dicyclohexyl carbodiimide. Only 1-(3-dimethylaminopropyl)-3-ethylcarbodiimide hydrochloride (EDC), however, has the proper reactivity and solubility to permit its use in an aqueous system, such as, the heparin coupling reaction of the present invention.

More particularly, in Inventive Embodiments I and II, dehydrating agents are used to facilitate the reaction in which the spacer is covalently bonded to the polymer backbone. Desirably, the chemical bond formed therebetween is either an amide or an amine chemical linkage. Similarly, dehydrating agents are used to facilitate the reaction in which the bio-active agent is covalently bonded to the polymer backbone via the spacer. In this reaction, the linkage between the spacer and the bio-active agent is an amide. Desirably, EDC catalyzes both of these reactions in the aqueous media of the present invention. In non-aqueous organic solvents many carbodiimides can be used, such as, for example, dicyclohexyl carbodiimide.

As Table 1 indicates, the present invention, e.g., Inventive Embodiments I and II, significantly improves upon previously described bio-active coating compositions and methods of making same, such as the Park Method described herein.

TABLE 1

|  | Park Method | Inventive Embodiment I | Inventive Embodiment II |
| --- | --- | --- | --- |
| Polymer Yield (gm/gm starting material) | 0.40 ± 0.5 | 1.05 ± 0.12 | 0.86 |
| Level of Polymer Cross-Linking | Moderate (1–60) | Negligible–Low (0–15) | Negligible–Low (0–25) |
| Factor Xa Heparin Activity μg/cm | 0.03–0.13 | 0.3–0.09 | 0.05 |

As illustrated in Table 1, the methods of the present invention provide for approximately a 100% increase in polymer yield while significantly decreasing the amount of polymer cross-linking, i.e. unwanted side-reactions and cross-sections, and without sacrificing heparin bio-activity. This surprising and unexpected result is believed, in part, to be attributable to the different addition sites in the present compositions compared to the prior art. In the present invention, all additions are made to reactive carbon atoms in the polymer backbone, whereas in Park, all additions to the polymer are made via reactive nitrogen atoms in the urethane linkage.

As used herein, the term "bio-active agent" is intended to mean any agent that is reactive with the present reactive nitrogen groups of the spacer to form a stable bond, is active upon introduction into a living system and enhances the bio-compatibility of any article introduced therein. Thus, the term "bio-active agent" includes anti-thrombogenic agents, such as, heparin, prostaglandins, urokinase, streptokinase, sulfated polysaccharide, albumin, etc., their pharmaceutical salts and mixtures thereof. In the present invention, "bio-active agent" also includes anti-infective agents including, for example, antibiotics, antibacterial agents, antiviral agents, antimicrobial agents, their pharmaceutical salts and mixtures thereof. The present invention also contemplates using mixtures of anti-thrombogenic agents and anti-infective agents.

In some cases it may be desirable to provide either dual anti-infective or anti-thrombogenic action with two or more agents. Additionally, it may be desirable to combine an anti-infective and an anti-thrombogenic action by combining two or more of these different agents. The invention will be described in terms of the preferred heparin, a known anti-thrombogenic agent of known safety and high anti-coagulation activity, with the understanding that the invention contemplates any anti-thrombogenic and/or anti-infective agent which may be grafted to the polymer backbone by the method of the present invention.

The bio-active agent of the present invention is bonded to the polymer backbone via a spacer group. The spacer group may include oxygenated polyolefins (e.g., polyvinyl alcohol), aliphatic polyesters, polyamino acids, polyamines, hydrophilic polysiloxanes, hydrophilic polysilazanes, hydrophilic acrylates, hydrophilic methacrylates, and linear or lightly branched polysaccharides. The spacer group is intended to be hydrophilic in order to take advantage of the natural repulsive forces of the hydrophobic substrate. The spacer group should have reactive functional groups on each end that are capable of reacting with and binding to the polymer backbone and bio-active agent respectively. Desirably, the spacer group has a functional group on each end, such as, carboxylic acid or a reactive nitrogen groups. More desirably, the spacer is an hydrophilic amino end-blocked poly(ethylene oxide).

Hydrophilic poly(ethylene oxide) spacers are suitable for use in the present invention because they have low interfacial free energy, lack binding sites, and exhibit highly dynamic motion. These characteristics are important because they increase the activity of a PEO-linked bio-active agent, e.g., heparin. See, K. D. Park et al., supra.

The length of the spacer group may be used to control the bio-active agent's activity. It is known in the art that the anti-thrombogenic activity of heparin is increased when it is positioned a certain distance from the substrate to which it is bound. For example, in a comparison of polymer-spacer-heparin coatings using a $C_6$ alkyl spacer, PEO 200, PEO 1000 and PEO 4000, the polymer-PEO 4000-Heparin surface maintained the highest bio-activity. See, K. D. Park et al., supra. Thus, methods are available in the art for controlling the activity of a polymer-bound bio-active agent. By utilizing such methods, one may determine the optimal length of the spacer. Accordingly, as used herein, "effective distance" or "bio-effective distance" means the distance between the bound bio-active agent and the polymer backbone which corresponds to a desired level of activity in the bio-active agent. In this way, the bio-active agent may be controlled simply be choosing the appropriate spacer.

Thus, in the present invention, control over the bio-active agent's activity is achieved by varying the length, e.g., molecular weight, of the spacer group. The spacer group may have a molecular weight of about 100 to about 200,000 daltons. Desirably, the spacer group has a molecular weight of about 200 to about 50,000 daltons. More desirably, the spacer group has a molecular weight of about 1,000 to about 10,000 daltons, such as for example, 4,000 daltons.

The presently described polymeric coatings can be applied to a variety of articles. An article of the invention may include any medical device compatible with a polymer bound bio-active agent coating which, absent the coating, may lead to thrombus formation and/or infection when in contact with a body tissue or fluid. Exemplary of, but not limited to, such articles are vascular access (arterial and venous) catheters, introducers, vascular grafts, endoprosthesis, stents, graft-stent combinations, urinary catheters and associated articles, such as drainage bags and connectors, and all abdominal cavity drainage tubing, bags and connectors. Desirably, the articles are polymeric, more desirably, they are expandable polytetrafluoroethylene (ePTFE) small caliber vascular grafts. For purposes of this invention, "vascular grafts" is meant to include endoprostheses.

Thus, an article of the present invention may be contacted with an aqueous solution containing one of the compositions of the present invention. All conventional methods of applying a coating to an article are contemplated by the invention. For example, the article may be dipped or steeped in such a solution, thus coating an appropriate surface of the article. Alternatively, a coating of one of the compositions of the invention may be sprayed onto a surface of the article. The surface to be coated with a composition of the present invention may be subjected to plasma treatment prior to application of one or more coats of the present invention. For example, the luminal surface of a small caliber ePTFE vascular graft may be prepared by treatment with a hydrogen-rich plasma followed by applying one or more coats of the invention.

Thus, a coating composition according to the present invention includes a biocompatible polymeric backbone having at least one pendant moiety. This polymeric structure is defined by structure VIII below:

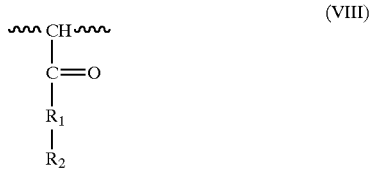

wherein $R_1$ and $R_2$ are a spacer group and bio-active agent, respectively as defined previously.

This coating can be applied to medical device, including grafts, stents and graft-stent combinations, as set forth above.

In another embodiment of the invention, a method is provided for preparing a bio-active polymer coating. This coating has a bio-active group covalently bonded through a spacer group to a polymer backbone. The present method includes providing a prepolymer backbone having a reactive functionality. As set forth previously, the reactive functionality includes for example, carboxylic acid functional groups, derivatives thereof, carbon atom-containing functional groups and mixtures thereof. A pendant group is then formed off of the prepolymer backbone by reacting the prepolymer with a spacer having reactive nitrogen groups. In this reaction, a carbon atom of the reactive functionality in the prepolymer forms a covalent bond with a reactive nitrogen group of the spacer in the presence of a first dehydrating agent. In a further reaction, one or more unreacted nitrogen groups of the spacer react with a bio-active agent in the presence of a second dehydrating agent to covalently bond the bio-active agent to the pendant group. A further step in this reaction can include applying the bio-active polymer coating to a medical device using any conventional method, including those previously described.

Another embodiment of the invention includes a bioactive coating composition. This bioactive coating composition includes a biocompatible polymer backbone, a spacer group and a bio-active agent. In this coating composition, the bio-active agent is pendant from the polymer backbone through the spacer group and the spacer group is covalently bonded to the polymer backbone through a reactive carbon atom in the polymer backbone. This coating composition is formed as described in detail above. The present invention further contemplates coating a variety of medical devices which are compatible with this bio-active agent.

The invention being thus described, it will be obvious that the same may be varied in many ways. Such variations are not to be regarded as a departure from the spirit and scope of the invention and all such modifications are intended to be included within the scope of the following claims.

What is claimed is:

1. A method for preparing a bio-active coating comprising:

providing a prepolymer backbone having a reactive functionality selected from the group consisting essentially of saturated and unsaturated carboxylic acid functional groups and mixtures thereof;

b) forming a pendent group off of said prepolymer backbone by reacting a carbon atom of said reactive functionality with a spacer, said spacer having reactive nitrogen groups, wherein said carbon atom forms a covalent bond with a reactive nitrogen group of said spacer in the presence of a first dehydrating agent; and c) reacting an unreacted nitrogen group of said spacer with a bio-active agent in the presence of a second dehydrating agent to covalently bond said bio-active agent to said pendent group.

2. The method of claim 1, wherein said spacer is selected from the group consisting of oxygenated polyolefins, aliphatic polyesters, polyamino acids, polyamines, hydrophilic polysiloxanes, hydrophilic polysilazanes, hydrophilic acrylates, hydrophilic methacrylates, linear and lightly branched polysaccharides.

3. The method of claim 1, wherein said spacer is an hydrophilic amino end-blocked poly(ethylene oxide).

4. The method of claim 3, wherein said hydrophilic amino end-blocked poly(ethylene oxide) has a molecular weight of about 100 daltons to about 200,000 daltons.

5. The method of claim 3, wherein said hydrophilic amino end-blocked poly(ethylene oxide) has a molecular weight of about 200 daltons to about 50,000 daltons.

6. The method of claim 3, wherein said hydrophilic amino end-blocked poly(ethylene oxide) has a molecular weight of about 1,000 daltons to about 10,000 daltons.

7. The method of claim 1, wherein said molecular weight of said spacer positions said bio-active agent at an effective distance from said polymer backbone.

8. The method of claim 1, wherein said bio-active agent is selected from the group consisting of anti-thrombogenic agents, antibiotic agents, antibacterial agents, antiviral agents, their pharmaceutical salts, and mixtures thereof.

9. The method of claim 1, wherein said bio-active agent is heparin.

10. The method of claim 1, wherein said first and second dehydrating agents are 1-(3-dimethylaminopropyl)-3-ethylcarbodiimide.

11. The method of claim 1, wherein said polymer backbone is selected from the group consisting of poly (urethanes), poly(carbomates), polyesters, polyethers and mixtures thereof.

12. The method of claim 1, further comprising the step of applying said bio-active polymer coating to a medical device.

13. A method for preparing a bio-compatible coating comprising:

a) providing a prepolymer backbone having reactive unsaturated carboxylic acid functional group;

b) reacting said unsaturated carboxylic acid functional group with a spacer compound having at least two reactive nitrogen atoms, and c) reacting a nitrogen atom of said spacer with a bio-active agent to bond said bio-active agent to said pendent group.

* * * * *